(12) United States Patent
Simon et al.

(10) Patent No.: US 10,254,785 B2
(45) Date of Patent: Apr. 9, 2019

(54) SYSTEM AND METHODS FOR THE SYNCHRONIZATION OF A NON-REAL TIME OPERATING SYSTEM PC TO A REMOTE REAL-TIME DATA COLLECTING MICROCONTROLLER

(71) Applicant: CERORA, INC., Bethlehem, PA (US)

(72) Inventors: Adam J. Simon, Yardley, PA (US);
Gary S. Kath, Scotch Pines, NJ (US);
David M. Devilbiss, Madison, WI (US)

(73) Assignee: Cerora, Inc., Bethlehem, PA (US)

( * ) Notice: Subject to any disclaimer, the term of this patent is extended or adjusted under 35 U.S.C. 154(b) by 120 days.

(21) Appl. No.: 15/323,249

(22) PCT Filed: Jun. 30, 2015

(86) PCT No.: PCT/US2015/038673
§ 371 (c)(1),
(2) Date: Dec. 30, 2016

(87) PCT Pub. No.: WO2016/004111
PCT Pub. Date: Jan. 7, 2016

(65) Prior Publication Data
US 2017/0177023 A1    Jun. 22, 2017

Related U.S. Application Data

(60) Provisional application No. 62/019,291, filed on Jun. 30, 2014.

(51) Int. Cl.
*G06F 1/14* (2006.01)
*G09C 1/00* (2006.01)
(Continued)

(52) U.S. Cl.
CPC .............. *G06F 1/14* (2013.01); *A61B 5/002* (2013.01); *A61B 5/0006* (2013.01);
(Continued)

(58) Field of Classification Search
None
See application file for complete search history.

(56) References Cited

U.S. PATENT DOCUMENTS

| 2002/0019586 A1 | 2/2002 | Teller et al. |
| 2002/0055687 A1 | 5/2002 | Lutz |

(Continued)

FOREIGN PATENT DOCUMENTS

| CN | 107847194 A | 3/2018 |
| WO | WO-2014085480 A1 | 6/2014 |
| WO | WO-2016004117 A1 | 1/2016 |

OTHER PUBLICATIONS

"A Procedure for Measuring Latencies in Brain-Computer Interfaces", IEEE Xplore | IEEE Periodicals | Jul. 1, 2010 | IEEE Transactions on Biomedical Engineering.*

(Continued)

*Primary Examiner* — Jaweed A Abbaszadeh
*Assistant Examiner* — Cheri L Harrington
(74) *Attorney, Agent, or Firm* — Schwegman Lundberg & Woessner, P.A.

(57) ABSTRACT

A system synchronizes a PC exhibiting latency of operations to a biosensor enabled microcontroller with real-time clock by providing an encoding scheme that captures the subject's absolute reaction time transmits the subject's reaction time from the PC exhibiting latency to the microcontroller with real-time clock. The system includes a transmitter that transmits a stimulus signal from the PC exhibiting latency, an input device indicating the subject's response to the stimulus signal, an encoding circuit adapted to encode a difference in time between the stimulus signal and the subject's response to the stimulus signal, an emitter adapted to transmit the encoded difference signal representing the subject's reaction time, and a complementary receiver adapted to detect the encoded difference signal. The receiver (Continued)

includes a decoding circuit that decodes the encoded difference signal to determine the subject's reaction time, and the receiver provides the subject's reaction time to the microcontroller with real-time clock for synchronization with received biosensor data such as EEG data.

10 Claims, 16 Drawing Sheets

(51) Int. Cl.

| | | |
|---|---|---|
| A61B 5/00 | (2006.01) | |
| A61B 5/0478 | (2006.01) | |
| A61B 5/0482 | (2006.01) | |
| A61B 5/0484 | (2006.01) | |
| H04L 29/08 | (2006.01) | |
| H04W 4/70 | (2018.01) | |
| A61B 5/16 | (2006.01) | |
| G16H 50/20 | (2018.01) | |
| A61B 5/024 | (2006.01) | |
| A61B 5/053 | (2006.01) | |
| A61B 5/1171 | (2016.01) | |
| A61B 5/12 | (2006.01) | |
| A61B 5/044 | (2006.01) | |

(52) U.S. Cl.
CPC ........ *A61B 5/0017* (2013.01); *A61B 5/02405* (2013.01); *A61B 5/0478* (2013.01); *A61B 5/0482* (2013.01); *A61B 5/0484* (2013.01); *A61B 5/0533* (2013.01); *A61B 5/1176* (2013.01); *A61B 5/125* (2013.01); *A61B 5/162* (2013.01); *A61B 5/163* (2017.08); *A61B 5/167* (2013.01); *A61B 5/168* (2013.01); *A61B 5/4803* (2013.01); *A61B 5/4884* (2013.01); *A61B 5/6803* (2013.01); *A61B 5/7405* (2013.01); *A61B 5/7475* (2013.01); *G09C 1/00* (2013.01); *G16H 50/20* (2018.01); *H04L 67/12* (2013.01); *H04W 4/70* (2018.02); *A61B 5/044* (2013.01); *A61B 5/16* (2013.01)

(56) References Cited

U.S. PATENT DOCUMENTS

| | | | |
|---|---|---|---|
| 2003/0181790 A1 | 9/2003 | David et al. | |
| 2004/0138578 A1 | 7/2004 | Pineda et al. | |
| 2005/0085744 A1* | 4/2005 | Beverina | A61B 5/486 600/558 |
| 2007/0191727 A1 | 8/2007 | Fadem | |
| 2009/0018458 A1* | 1/2009 | Cao | A61B 5/04004 600/509 |
| 2009/0024050 A1 | 1/2009 | Jung et al. | |
| 2009/0088608 A1 | 4/2009 | Mumford et al. | |
| 2010/0174533 A1 | 7/2010 | Pakhomov | |
| 2010/0312508 A1 | 12/2010 | Mott et al. | |
| 2011/0027766 A1* | 2/2011 | Yoo | A61H 5/00 434/262 |
| 2011/0152629 A1 | 6/2011 | Eaton et al. | |
| 2011/0184307 A1* | 7/2011 | Hulin | A61B 5/0006 600/544 |
| 2011/0224571 A1 | 9/2011 | Pascual-Leone et al. | |
| 2011/0282232 A1 | 11/2011 | Pradeep et al. | |
| 2012/0253220 A1 | 10/2012 | Rai et al. | |
| 2012/0274906 A1 | 11/2012 | Privitera et al. | |
| 2013/0035579 A1 | 2/2013 | Le et al. | |
| 2013/0274626 A1* | 10/2013 | Chang | A61B 5/7285 600/558 |
| 2014/0012509 A1* | 1/2014 | Barber | G06F 3/015 702/19 |
| 2014/0128735 A1 | 5/2014 | Newell et al. | |
| 2014/0148728 A1 | 5/2014 | Eizenman et al. | |
| 2014/0180060 A1 | 6/2014 | Parrish et al. | |
| 2015/0257967 A1 | 9/2015 | Simmons | |
| 2015/0261936 A1* | 9/2015 | Zhou | A61B 5/04012 705/3 |
| 2016/0000348 A1* | 1/2016 | Kitajo | A61B 5/726 600/545 |
| 2016/0022167 A1* | 1/2016 | Simon | A61B 5/04842 600/301 |
| 2016/0029962 A1 | 2/2016 | Hyde et al. | |
| 2016/0029965 A1 | 2/2016 | Simon | |
| 2016/0235323 A1* | 8/2016 | Tadi | A61B 5/7285 |
| 2017/0020406 A1* | 1/2017 | Chiouchang | A61B 5/7285 |
| 2017/0249280 A1* | 8/2017 | Wu | G06F 13/4282 |
| 2018/0184964 A1 | 7/2018 | Simon et al. | |

OTHER PUBLICATIONS

"A Synchronization Method for Wireless Acquisition Systems, Application to Brain Computer Interfaces", IEEE Xplore | IEEE Conferences | Jul. 1, 2013 | 2013 35th Annual International Conference of the IEEE Engineering in Medicine and Biology Society (EMBC) (pp. 830-833).*

Belger et al., "The Neural Circuitry of Autism", Neurotox Res, 2011, 20, 201-214.

Duffy et al., "A stable pattern of EEG spectral coherence distinguishes children with autism from neuro-typical controls—a large case control study", BMC Medicine, 2012, 10:64, 18 pages.

Fishmean et al., "Contrasting patterns of language-associated brain activity in autism and Williams syndrome", Social Cognitive and Affective Neuroscience. Oct. 2011, 10 pages.

Moseley et al., "Brain Routes for Reading in Adults with and without Autism: EMEG Evidence", J Autism Dev Disord, 2014, 44, 137-153.

Patriquin et al., "Respiratory sinus arrhythmia: A marker for positive social functioning and receptive language skills in children with autism spectrum disorders", Developmental Psychobiology, 2015, 13 pages.

Pierce et al., "The brain response to personally familiar faces in autism: findings of fusiform activity and beyond", Brain, Jan. 2005, 15 pages.

Sasson et al., "Eye Tracking Young Children with Autism", Journal of Visualized Experiments, Mar. 2012, 61, e3675, 7 pages.

"U.S. Appl. No. 15/323,238, Non Final Office Action dated Sep. 6, 2018", 22 pgs.

"U.S. Appl. No. 15/323,238, Preliminary Amendment filed Dec. 30, 2016", 3 pgs.

"European Application Serial No. 15814892.4, Extended European Search Report dated Jan. 30, 2018", 7 pgs.

"International Application Serial No. PCT/US2015/038673, International Preliminary Report on Patentability dated Jan. 12, 2017", 6 pgs.

"International Application Serial No. PCT/US2015/038673, International Search Report dated Nov. 15, 2015", 2 pgs.

"International Application Serial No. PCT/US2015/038673, Written Opinion dated Sep. 15, 2015", 4 pgs.

"International Application Serial No. PCT/US2015/038684, International Preliminary Report on Patentability dated Jan. 12, 2017", 8 pgs.

"International Application Serial No. PCT/US2015/038684, Written Opinion dated Sep. 24, 2015", 3 pgs.

"International Application Serial No. PCT/US2015/038684, Written Opinion dated Sep. 24, 2015", 6 pgs.

Adam, Wilson J, et al., "A Procedure for Measuring Latencies in Brain-Computer Interfaces", IEEE Transactions on Biomedical Engineering, vol. 57, No. 7, (Jul. 1, 2010), 1785-1797.

Chris, Otto, "An implementation of a wireless body area network for ambulatory health monitoring", ProQuest Dissertations Publishing, (May 4, 2006).

Fishman, Inna, et al., "Contrasting patterns of language-associated brain activity in autism and Williams syndrome", SCAN, (2011), 9 pgs.

(56) References Cited

OTHER PUBLICATIONS

Moseley, R L, et al., "Brain Routes for Reading in-Adults with and without Autism: EMEG Evidence", J Autism Dev Disord, (Jun. 9, 2013), 17 pgs.

Patriquin, Michelle, et al., "Respiratory Sinus Arrhythmia: A Marker for Positive Social Functioning and Receptive Language Skills in Children with Autism Spectrum Disorders", Developmental Psychobiology, (Dec. 27, 2011), 12 pgs.

Pierce, Karen, et al., "The Brain Response to Personally Familiar Faces in Autism: Findings of Fusiform Activity and Beyond", Brain, (Aug. 19, 2004), 14 pgs.

* cited by examiner

Laptop computer with visual stimulus and sync trigger dot image

Light sensor circuitry to detect LCD trigger-dot and mouse-click and transmit reaction pulse via wireless interface (RF, Optical, Ultrasonic) to EEG Headset Hardwired interface to mouse to pickup real-time mouse-click Digital and wireless carrier signals used to send reaction time to EEG Headset EEG Headset wireless receiver used to capture wireless reaction-time signal for synchronization with EEG data Reaction time signal received at EEG Headset synchronized with the EEG Signal Light-Sensor and lens mounted inside EEG
Headset capturing light from computer LCD Stylus interface for use with Tablet PC Microphone capturing sound from computer speaker Earbud audio signal detection Patient response via finger-tap on the EEG Headset accelerometer Means of encoding "right" or "left" mouse click into On/Off Keyed Wireless Signal

SYSTEM AND METHODS FOR THE SYNCHRONIZATION OF A NON-REAL TIME OPERATING SYSTEM PC TO A REMOTE REAL-TIME DATA COLLECTING MICROCONTROLLER

CROSS REFERENCE TO RELATED APPLICATIONS

This application is a National Stage Application filed under 35 U.S.C. § 371 of International Application No. PCT/US2015/038673, filed Jun. 30, 2015, which claims priority benefit of U.S. Provisional Patent Application No. 62/019,291 filed Jun. 30, 2014. The contents of both patent applications are hereby incorporated by reference in their entireties.

TECHNICAL FIELD

The invention relates to hardware and systems to synchronize the presentation of stimuli and probes on a commercial PC with a standard but non-real-time operating system such as Windows, Linux, Android, or iOS with the precision clock in a real-time data acquisition in an embedded microcontroller.

BACKGROUND

The precise timing of a patient stimulus and patient response in reference to the EEG data collected during brain assessment is important for diagnosis evaluation. Imprecise timing would not allow the proper data segment of the EEG trace to be time-synchronized with the actual stimulus/response event.

The function of a data collection engine is to collect data from each of the biosensors, human interface devices (HID) devices (including keystrokes and mouse/touchpad/touch screen events), and to provide synchronous time-stamping of data streams. The data collection engine will also communicate with the REM to receive data packet stream (e.g. via Bluetooth or Wi-Fi) and send configuration commands and stimulus data (e.g. audio files). The data collection engine will also provide timestamps for all output stimuli (video display). This module must have the highest priority of any program running on the device to ensure precise and accurate time stamping of all data is an incoming and outgoing.

For example, the interval between a mouse click, a keyboard switch contact, or a touchpad event and the software assigned timestamp must occur with the same latency for each event of that type. Additionally, the software generated timestamp of a mouse click must align precisely with the EEG data sample timestamps. Furthermore, the timestamp for a stimulus (such as display of an object on the video screen) must be accurately synchronized to input data streams. This will allow the ability to identify the exact EEG data sample that occurred during another input event (e.g. mouse click) or a stimulus event (e.g. video display event). When data collection is controlled with this level of precision, then differences in latencies across devices become less critical.

In non-deterministic environments the most critical thing is that jitter is minimized, not latency.

Generally, a computer server that collects biosensor data provides a ring buffer for client access functions as well as a storage buffer in volatile and memory or encrypted flat files. A data collection engine leverages the security/data encryption module to store data locally or retain in volatile memory (RAM) and transmits encrypted data to a cloud API using a cloud communications module. The I/O module will also allow other client software components access to the data stream. The server will also allow external devices to connect to the ring buffer for read only access.

For Windows operating systems there are a number of software products that allow an engine such as this to run in real-time or with real-time threads. On such product is the INTime for Windows by tenAsys described at: http://www-.tenasys.com/overview-ifw.

With the Android operating system, this is much more difficult without rooting the device and replacing the kernel or the scheduler. However, with the newest version of Android OS and a number of software modifications, one may be able to create a near real-time data collection device. See, for example Mondia B S and Mdisetti V K, Reliable RealpTime Applications on Android OS, Georgia Tech, submitted 2010).

Currently, two levels of precision have been defined for the data collection engine.

Level 1: Timestamp precision of better than 10 milliseconds resolution. Most if not all functions will be at this level. For example, the time-stamping precision between keyboard events and EEG data-sample timestamps need to be less than 10 milliseconds. Specifically, a keyboard event will be time-stamped within 10 milliseconds of the EEG data sample with which it occurred.

Level 2: Timestamp precision within or less than one millisecond. This level of precision is reserved for two fundamental tasks: an audio evoked response potential (ERP) task and two reaction time tasks. At this level, a data sample timestamp must be synchronized across input streams within 1 millisecond. For example, with the audio ERP task, the start of an audio tone must occur and be time-stamped within 1 millisecond of the EEG data-sample with which it co-occurred. A second example is the reaction time task. Here, a mouse button press, keyboard press, or touch screen event must be time-stamped with a precision of 1 millisecond relative to the onset of an image on the screen. This level of precision is critical because human reaction times are measured on the millisecond or sub-millisecond scale.

Currently this level of precision is possible on a PC. However, this level of precision may not be possible on an Android tablet given that touch events are synchronized to the Vsync interrupt at 60 frames per second, which corresponds to a 16 millisecond resolution.

It is desired to synchronize the presentation of stimuli and probes on a commercial PC with a standard but non-real-time operating system such as Windows, Linux, Android, or iOS so that data may be acquired in real-time. The invention addresses these and other needs in the art.

SUMMARY

The invention includes systems that synchronize the presentation of stimuli and probes on a commercial PC with a standard but non-real-time operating system such as Windows, Linux, Android, or iOS with the precision clock in a real-time data acquisition embedded microcontroller. Paired emitter/receivers and encoding software implemented on the processing device may also be provided to precisely synchronize in time an operating system of the processing device with a real-time environment set by a real-time clock of the processing device receiving biosensor outputs at inputs thereof.

An exemplary embodiment of the system synchronizes a PC exhibiting latency of operations to a biosensor enabled microcontroller with real-time clock by providing an encoding scheme that captures the subject's absolute reaction time transmits the subject's reaction time from the PC exhibiting latency to the microcontroller with real-time clock. The system includes a transmitter that transmits a stimulus signal from the PC exhibiting latency, an input device indicating the subject's response to the stimulus signal, an encoding circuit adapted to encode a difference in time between the stimulus signal and the subject's response to the stimulus signal, an emitter adapted to transmit the encoded difference signal representing the subject's reaction time, and a complementary receiver adapted to detect the encoded difference signal. The receiver includes a decoding circuit that decodes the encoded difference signal to determine the subject's reaction time, and the receiver provides the subject's reaction time to the microcontroller with real-time clock for synchronization with received biosensor data such as EEG data.

In exemplary embodiments, the emitter comprises a visible LED, an ultrasonic transducer, an infrared (IR) LED, an audible speaker, audible transducer, a Bluetooth transmitter/transceiver, a Wifi transmitter/transceiver, a ZigBee transmitter/transceiver or AM or FM transmitter/transceiver, while the complementary receiver comprises a visible photodiode, visible phototransistor, an ultrasonic receiver/microphone, an infrared (IR) photodiode, an infrared phototransistor, an audible microphone, a Bluetooth receiver/transceiver, a Wifi receiver/transceiver, a ZigBee receiver/transceiver, an AM receiver/transceiver, or an FM receiver/transceiver.

The input device may be a mouse that provides an input to the encoding circuit. The encoding circuit is also responsive to the stimulus signal from the transmitter and encodes the difference signal as an on/off keyed wireless signal that is provided to the emitter for wireless transmission to the complementary receiver. In exemplary embodiments, the encoding circuit also may encode a left mouse click as one keyed pulse and a right mouse click as two keyed pulses.

In exemplary embodiments, the complementary receiver is located at an EEG headset of the subject. The EEG headset includes the decoding circuit and the microcontroller for synchronizing the subject's reaction time to EEG data collected by the EEG headset. In such embodiments, the emitter may comprise an audible speaker and the receiver may comprise an earbud of the subject, where the earbud provides received sound signals to the decoding circuit. The EEG headset also may be adapted to include a finger tap input as the input device.

In other embodiments, the input device may a stylus and the PC exhibiting latency may be a tablet PC.

BRIEF DESCRIPTION OF THE DRAWINGS

Embodiments of the invention can be better understood with reference to the following drawings, of which.

DETAILED DESCRIPTION OF ILLUSTRATIVE EMBODIMENTS

Figure 1:
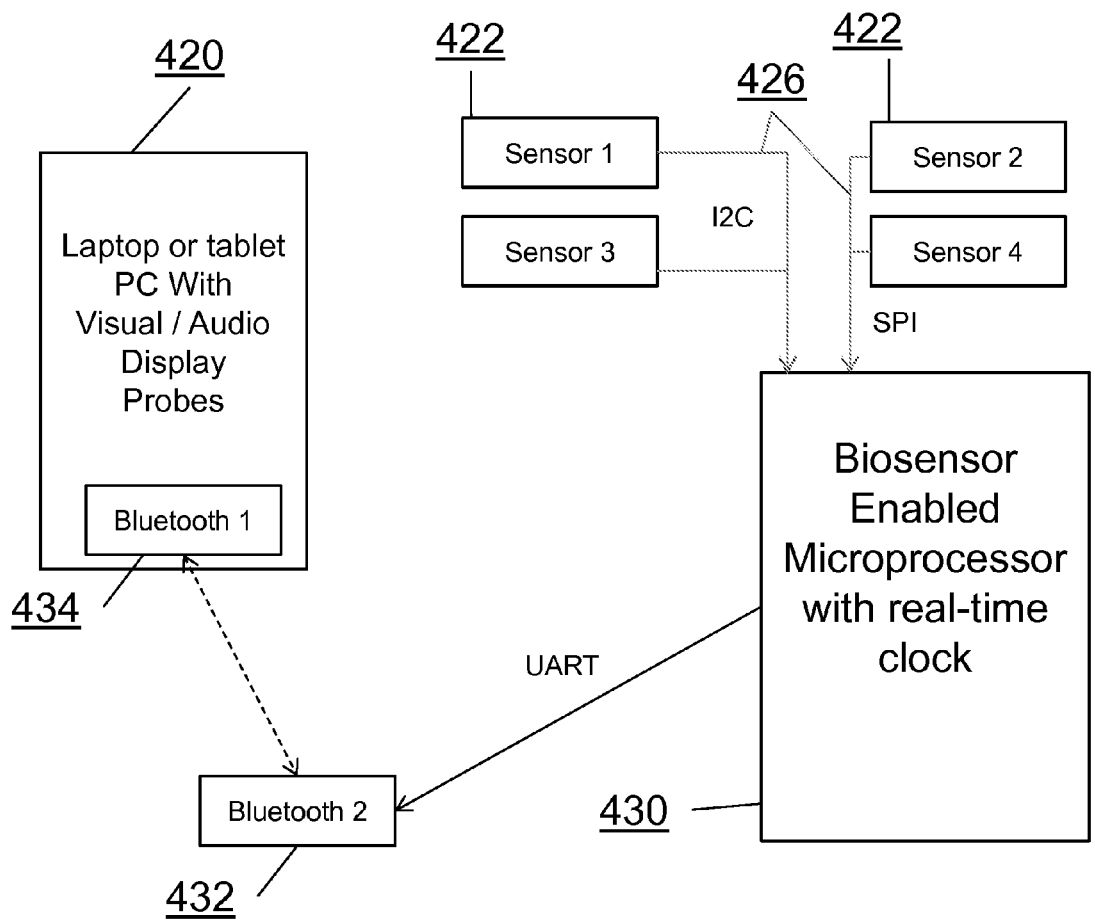
FIG. 1 is a schematic illustration showing a PC for task/probe display and stimulation while a microprocessor collects biosensor data from multiple sensors in a real-time environment.

The invention will be described in detail below with reference to FIGS. 1-16. Those skilled in the art will appreciate that the description given herein with respect to those figures is for exemplary purposes only and is not intended in any way to limit the scope of the invention. All questions regarding the scope of the invention may be resolved by referring to the appended claims.

Definitions

By "electrode to the scalp" we mean to include, without limitation, those electrodes requiring gel, dry electrode sensors, contactless sensors and any other means of measuring the electrical potential or apparent electrical induced potential by electromagnetic means.

By "monitor the brain and nervous system" we mean to include, without limitation, surveillance of normal health and aging, the early detection and monitoring of brain dysfunction, monitoring of brain injury and recovery, monitoring disease onset, progression and response to therapy, for the discovery and optimization of treatment and drug therapies, including without limitation, monitoring investigational compounds and registered pharmaceutical agents, as well as the monitoring of illegal substances and their presence or influence on an individual while driving, playing sports, or engaged in other regulated behaviors.

A "medical therapy" as used herein is intended to encompass any form of therapy with potential medical effect, including, without limitation, any pharmaceutical agent or treatment, compounds, biologics, medical device therapy, exercise, biofeedback or combinations thereof.

By "EEG data" we mean to include without limitation the raw time series, any spectral properties determined after Fourier or other transformation into the frequency domain, any nonlinear properties after non-linear analysis, any wavelet properties, any summary biometric variables and any combinations thereof.

A "sensory and cognitive challenge" as used herein is intended to encompass any form of sensory stimuli (to the five senses), cognitive challenges (to the mind), and other challenges (such as a respiratory $CO_2$ challenge, virtual reality balance challenge, hammer to knee reflex challenge, etc.).

A "sensory and cognitive challenge state" as used herein is intended to encompass any state of the brain and nervous system during the exposure to the sensory stimuli and cognitive load challenge.

An "electronic system" as used herein is intended to encompass, without limitation, hardware, software, firmware, analog circuits, DC-coupled or AC-coupled circuits, optical circuits, digital circuits, FPGA, ASICS, visual displays, audio transducers, temperature transducers, olfactory and odor generators, or any combination of the above.

By "spectral bands" we mean without limitation the generally accepted definitions in the standard literature conventions such that the bands of the PSD are often separated into the Delta band ($f<4$ Hz), the Theta band ($4<f<7$ Hz), the Alpha band ($8<f<12$ Hz), the Beta band ($12<f<30$ Hz), and the Gamma band ($30<f<100$ Hz). The exact boundaries of these bands are subject to some interpretation and are not considered hard and fast to all practitioners in the field.

By "calibrating" we mean the process of inputting known signals into the system and adjusting internal gain, offset or other adjustable parameters in order to bring the system to a quantitative state of reproducibility.

By "conducting quality control" we mean conducting assessments of the system with known input signals and verifying that the output of the system is as expected. Moreover, verifying the output to known input reference signals constitutes a form of quality control which assures that the system was in good working order either before or just after a block of data was collected on a human subject.

By "biomarker" we mean an objective measure of a biological or physiological function or process.

By "biomarker features or metrics" we mean a variable, biomarker, metric or feature which characterizes some aspect of the raw underlying time series data. These terms are equivalent for a biomarker as an objective measure and can be used interchangeably.

By "non-invasively" we mean lacking the need to penetrate the skin or tissue of a human subject.

By "diagnosis" we mean any one of the multiple intended use of a diagnostic including to classify subjects in categorical groups, to aid in the diagnosis when used with other additional information, to screen at a high level where no a priori reason exists, to be used as a prognostic marker, to be used as a disease or injury progression marker, to be used as a treatment response marker or even as a treatment monitoring endpoint.

By "electronics module" or "EM" or "reusable electronic module" or "REM" or "multi-functional biosensor" or "MFB" we mean an electronics module or device that can be used to record biological signals from the same subject or multiple subjects at different times. By the same terms, we also mean a disposable electronics module that can be used once and thrown away which may be part of the future as miniaturization becomes more common place and costs of production are reduced. The electronics module can have only one sensing function or a multitude (more than one), where the latter (more than one) is more common. All of these terms are equivalent and do not limit the scope of the invention.

By "biosignals" or "bio signals" or "bio-signals" we mean any direct or indirect biological signal measurement data streams which either directly derives from the human subject under assessment or indirectly derives from the human subject. Non-limiting examples for illustration purposes include EEG brainwave data recorded either directly from the scalp or contactless from the scalp, core temperature, physical motion or balance derived from body worn accelerometers, gyrometers, and magnetic compasses, the acoustic sound from a microphone to capture the voice of the individual, the stream of camera images from a front facing camera, the heart rate, heart rate variability and arterial oxygen from a would pulse oximeter, the skin conductance measured along the skin (Galvonic Skin Conductance/Resistance, also called Electrodermal Activity), the cognitive task information recorded as keyboard strokes, mouse clicks or touch screen events. There are many other biosignals to be recorded as well.

By "microprocessor" or "microcontroller" we mean any computational oriented silicon or other integrated circuit technology that includes a microprocessor along with or without direct storage RAM, including non-limiting illustrative examples as a 16-bit TI MSP430 or a 32-bit ARM Cortex M0 or M4 microcontroller from Freescale, STMicro, or other manufacturer.

By "jittery PC with latency" we mean any commercial computing device with an operating system that is able to go off and do activities and tasks that the user cannot control (such as garbage collection) and is not considered a "real-time operating system" (RTOS) as conventionally known in the embedded microcontroller community. This would include most commercial PCs including desktops, laptops, tablets and smartphones running standard versions of Microsoft Windows, Linux, Google's Android operating system or Apple's iOS operating system. The exception would be a device installed with a real-time operating system whereby all event control is provided to the engineer and user and none kept by the device manufacturer and operating system creator.

By "Real-Time Clock" we mean any time keeping implementation that generates a high-precision and high-accuracy time facility that will allow deterministic time-stamping of events by firmware or software with low computational overhead. As a non-limiting example, high-precision could be understood as timing intervals less than 0.1 milliseconds whereas high-accuracy could be understood as +/−5 PPM.

A System of Multiple Transducers to Both Stimulate and Record Physiological and Brain Response as a Periodic Biosensor Assessment for Brain Related Issues The systems and methods of the invention comprise multiple transducers to both stimulate and record the physiological response of the brain and the body in order to assess its health and function. Central to the system is the ability to directly record brainwave activity from an electrode place non-invasively on or near the scalp. Moreover, additional information on brain health and function can be derived from transducers that measure position and motion, temperature, cardiovascular properties like heart rate, heart rate variability, and arterial oxygen, as well as cognitive information, speech, eye movement, and surface skin conductance to name a few non-limiting additional biological signal measurement data stream examples. It is often necessary to bring the system to the human subject, getting out of the hospital or doctor's office and enabling data collection in the home or sports field or combat theater, thus providing accessibility to the brain health and function assessment from a lightweight and portable form factor. Moreover, it would be advantageous to have a minimal cost associated with the system so that it can be used around the globe to help those in need of brain health and function assessments.

A solution to these problems includes the creation of a system of body worn or body proximal electronic modules (EMs) or reusable electronic modules (REMs) with the ability to both record biological signal measurement data streams (biosensor data) as well as present stimuli to the human subject in the form of various sensory and cognitive challenges and tasks. In particular, one such electronic module (EM) or reusable electronic module (REM) can be placed in the vicinity of the head and be either reused over and over if it does not touch the human body or disposed of if it comes in direct contact with the human body.

Precision Synchronization Need Between Peripheral PC and Microcontroller with Biosensor Inputs A peripheral computer system (typically laptop or tablet PC but includes smartphone and other intermediate form factors) is used to administer a human subject's brain health assessment including various biosensors to record physiological parameters and streams of biosensor data. It can also include temporal measures of a subject's reaction time when presented with a sensory stimulus (i.e. video, acoustic) and records the subject's response via the computer or other input device (i.e. mouse, stylus, keyboard, microphone, accelerometer, etc.) as it measures the reaction time between stimulus presentation and the subject's response via the peripheral computer's clock. The precision and repeatability of the reaction time measurement is typically dependent on a commercial multi-tasking operating system which can introduce timing errors due to software latency and timing jitter (e.g. Microsoft Windows, Linux, Google Android, or Apple iOS).

The present invention describes a low-cost and simple to implement electronic hardware solution which can attach to the peripheral computer system. In one particular embodiment, the invention provides real-time time-stamping between the patient's stimulus, the patient's response and other biosensor data that is streaming from the human subject to an embedded microcontroller with a real-time clock, capable of synchronizing the various data packets at a much higher rate (less than 1 millisecond and perhaps as fast 0.1 microsecond) and greater temporal precision than a commercial multi-tasking OS not designed as a real-time operating system (RTOS).

The real-time hardware system in an exemplary embodiment includes a sensor that detects when a stimulus is generated by the computer system or presented to the subject, a second sensor to sense the subject's response, and a microcontroller to precisely record the response time with microsecond resolution. In addition, the invention provides a synchronization signal to the biosensor measurement system enabling a time-lock the biosensor data to the stimulus/response event in the peripheral PC.

It is often difficult to synchronize the presentation of stimuli and probes on a commercial PC (desktop, laptop, or tablet, or smartphone) with temporal resolution greater than the latency of the inherent fluctuations in the operating system on the PC (most often Windows, Linux, Android or iOS). The present invention is a solution which can temporally synchronize the probes and stimuli on the laptop PC with the biosensor system using various encoding schemes.

Temporally Precise Means to Synchronize Stimuli/Probes on a Jittery PC with Latency with Biosensor Data Streams Attached to an Embedded Microcontroller with Real-Time Clock One embodiment of the invention is illustrated in FIG. 1. In this embodiment, if the array of biosensors attached to the subject were all integrated into the inputs of an embedded microcontroller using local serial data buses, such as I2C or SPI or UART or wireless connections such as Bluetooth, WiFi or ZigBee, the real-time clock of the microcontroller could keep microsecond precision (or better) between the various biosensor data streams. In particular, popular microcontrollers such as the Texas Instruments MSP430 series or the ARM Cortex series could be utilized. What is difficult to do is to synchronize the probe presentation on the commercial PC with the real-time clock of the embedded microcontroller.

Consider FIG. 1, where a laptop or tablet PC with visual and audio display probes 420 is connected via Bluetooth module 1 (434) to Bluetooth module 2 (432). The various sensors 422 are combined into one and I2C or alternatively SPI digital bus 426 provide the biosensor data to the micro controller with real time clock 430. The biosensor enabled microcontroller with real time clock 430 is interfaced to Bluetooth module 2 (432) via a UART interface, which completes the loop to Bluetooth radio 1 (434), a part of the PC or tablet 420.

One could periodically on the PC side output a signal from the PC 420 that could be sensed by a sensor connected to the embedded microprocessor with a real-time clock 430. As a first non-limiting example, the PC sound card could emit a short 20 millisecond burst of sine waves of various frequencies. The first burst at the first second could be 1010 Hz so that 20 periods could be broadcast in the short 20 millisecond transmission. In the next burst a second later, the frequency could be 1020 Hz, the third emission could be 1030 Hz, etc. Thus, after N seconds, the frequency would be encoded to contain 1000 Hz+N*10 Hz. If N=120 seconds, then the last burst would contain 1000 Hz+120*10 Hz=2200 Hz. In this fashion, a microphone sensor attached to the embedded microprocessor could be used to precisely adjust for latency in the variable PC operating system.

Generally speaking, information transfer from the peripheral PC to the microcontroller will require energy to be transmitted from the PC to the microcontroller. This energy can be in the form of an electrical signal if hardwired or alternately in the form of light (photons), sound waves, radio transmission (RF). Other forms of energy can be contemplated as well. Sub-forms can further be segmented as well, such as photons that can be visible or UV or infrared. In the case of sound waves, they can be audible to a human or ultrasonic.

Figure 2:
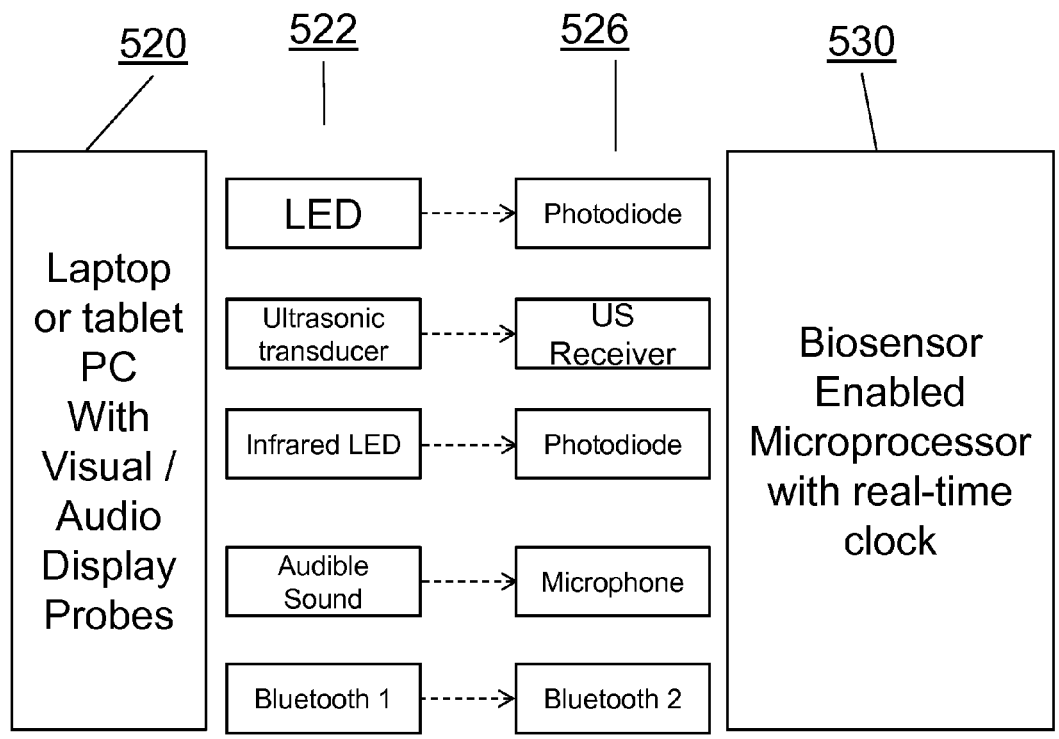
FIG. 2 is a schematic illustration of the use of emitter/receiver pairs (LED/photodiode), ultrasonic transducer/US receiver, infrared LED/photodiode, Audible sound/microphone, and a pair of Bluetooth modules to synchronize jitter and latency in the PC operating system with the real-time data collection of the microprocessor.

An alternate embodiment can be seen in FIG. 2 where one could use any one of the emitters 522 attached to PC 520 to emit energy which would be detected by sensor 526 directly connected to the biosensor enabled microprocessor/microcontroller 530 with a real-time clock and operating system. In an exemplary embodiment, an LED attached to the PC 520 acts as the emitter and a photodiode or other light receiver is attached to the embedded microcontroller 530. Similar to the sound based encoding scheme, the light based encoding scheme could modulate fiducial signals from the PC to a specially included sensor into the inputs of the microprocessor 530, thereby independently and precisely measuring the relative position in time of the probe/stimuli on the PC 520 with the recorded biosensor signals. As light travels much faster than sound, this would be even more precise but is not necessarily required.

Alternate embodiments are self-apparent and include use of ultrasound waves via an ultrasonic transducer in the 20-50 KHz range which is inaudible to humans but easily broadcast and measured with modern emitters and receivers. Small emitter devices could be plugged into the USB, headphone output and other analog and digital outputs of the PC 520 which are then coupled to particular biosensors included in the microprocessor 530 in order to temporally synchronize the PC with the recording biosensor array.

Alternate embodiments include the use of an infra-red LED (wavelengths shorter than the eye can see) with an appropriate IR photodiode to receive the transmitted light, audible sounds and an audible microphone, or even a first Bluetooth radio 1 and a second Bluetooth radio 2.

Figure 3:
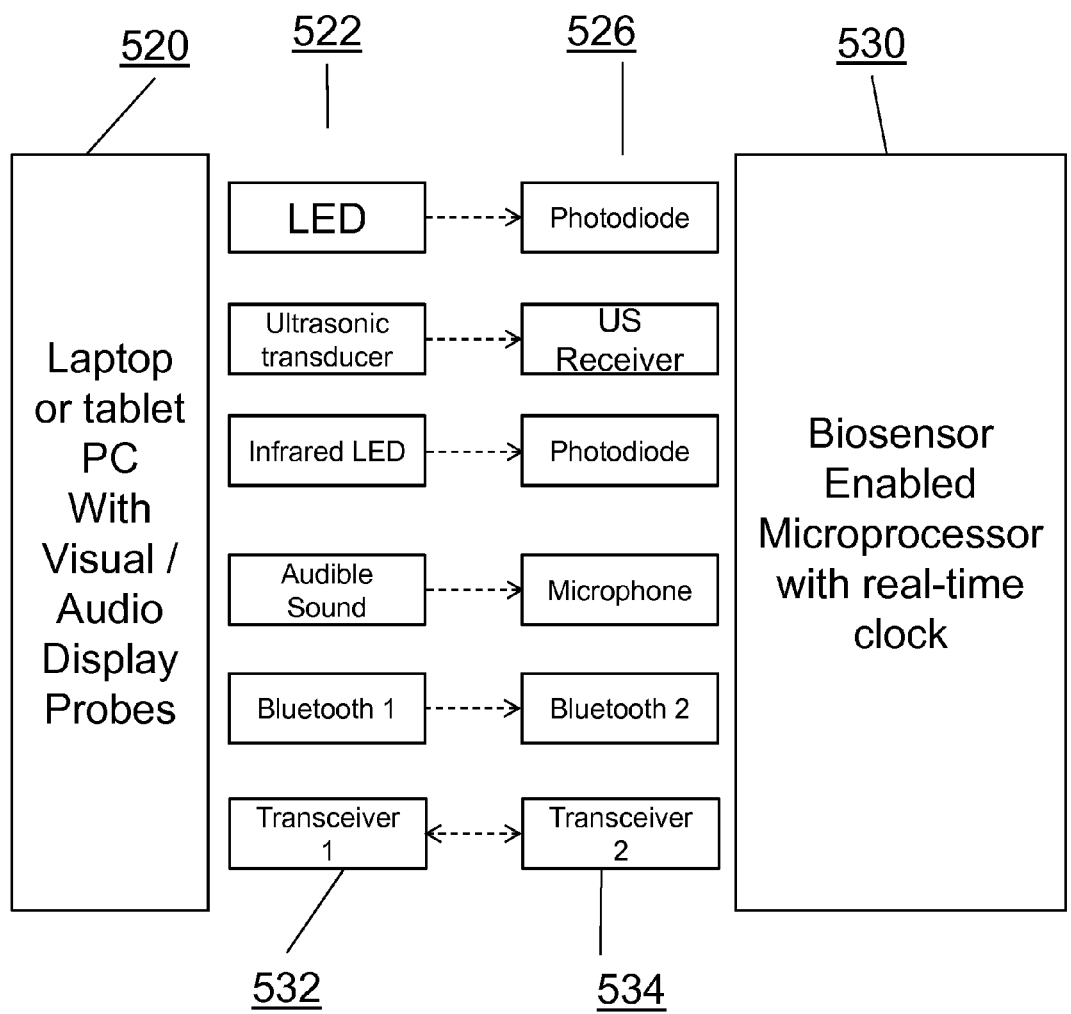
FIG. 3 is a schematic illustration generalizing the use of emitter/receiver pairs (LED/photodiode), ultrasonic transducer/US receiver, infrared LED/photodiode, Audible sound/microphone, a pair of Bluetooth modules, or any other "transceiver 1" and "transceiver 2" to synchronize jitter and latency in the PC operating system with the real-time data collection of the microprocessor.

As can be seen in FIG. 3, this paired emitter-receiver approach can be generalized by the inclusion of Transceiver 1 (532) attached to the PC 520 with latency and Transceiver 2 (534) attached to the real-time embedded microprocessor 530.

Visual Stimulus—Mouse Click Response Hardware

Figure 4:
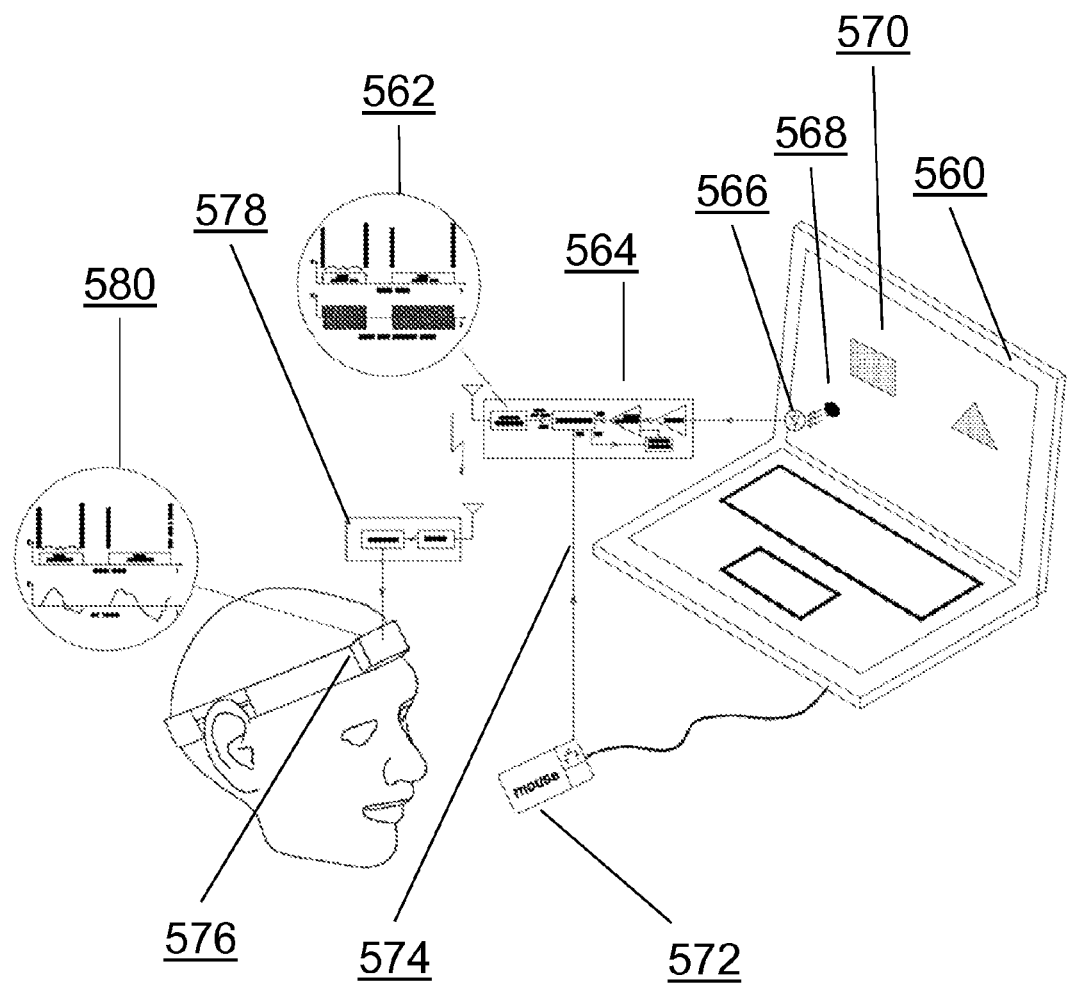
FIG. 4 is a schematic illustration of the use of overall system of synchronization to reduce jitter and latency between a commercial PC and the multimodal collection of real-time data collection within a microcontroller based acquisition system.

The hardware for a visual stimulus and mouse click response computer system, as illustrated in FIG. 4, includes a light sensor 566 (i.e. photodiode, photo transistor, photocell, photo-resistor) which attaches to the computer's screen 570 (i.e. LCD, touchscreen). The light sensor 566 is positioned in the corner of the screen such that it does not block the main view of the computer's screen. The light sensor 566 could be attached by means of a suction-cup, clip, tape or other means. The light sensor 566 would be shrouded to prevent stray room light from shinning on the detector to insure the sensor is only detecting light from the computer display.

When the visual stimulus is presented to the patient, a small dot 568 is also simultaneously illuminated on the computer display 570 under the light sensor 566. The light sensor signal 580 would be amplified by amplifier 582 (FIG. 6) and pulse shaped by a voltage comparator 584. A reference voltage 583 sets the light intensity threshold. This reference could be automatically adjusted via an analog output from the microcontroller 586. The light sensor 580 and voltage comparator 584 circuitry will present a precision trigger signal to the microcontroller 586 thereby signaling the start-time of the visual stimulus. The microcontroller would immediately activate a digital output 588 logic high signaling the start of the stimulus. Wireless transmitter 590 then provides the digital output 588 to antenna 592 for transmission.

To sense the patient's response, a customized mouse 572 (FIG. 4) is used. The microcontroller would monitor the switch contact 600 (FIG. 7) of the computer mouse. When the subject responds to the stimulus by clicking the mouse button, the microcontroller would reset the digital output 588 to logic low to signal the precise time the patient's reaction response occurred. The pulse width of the digital output 610 (FIG. 8) would represent the subject's reaction time and the leading edge 612 (FIG. 8) would indicate the start time of the visual stimulus.

Figure 8:
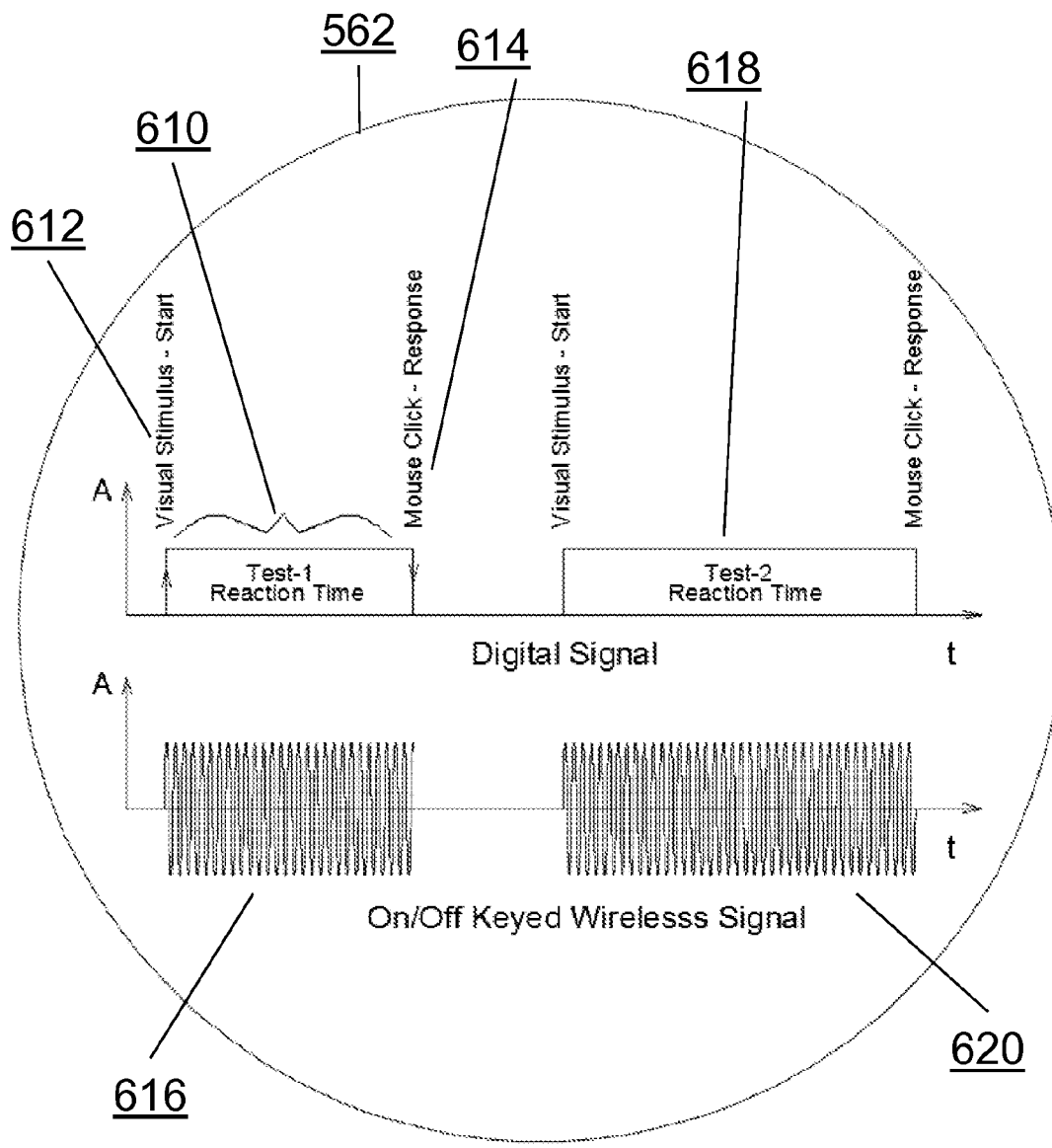
FIG. 8 is a schematic illustration of the temporal synchronization of a PC with a real-time data collection microcontroller with an upper time trace showing the human subject's actions while the lower time trace shows the transmission of a wireless signal at high frequency which corresponds to the leading and falling edge of the human subject's interactions.
Figure 9:
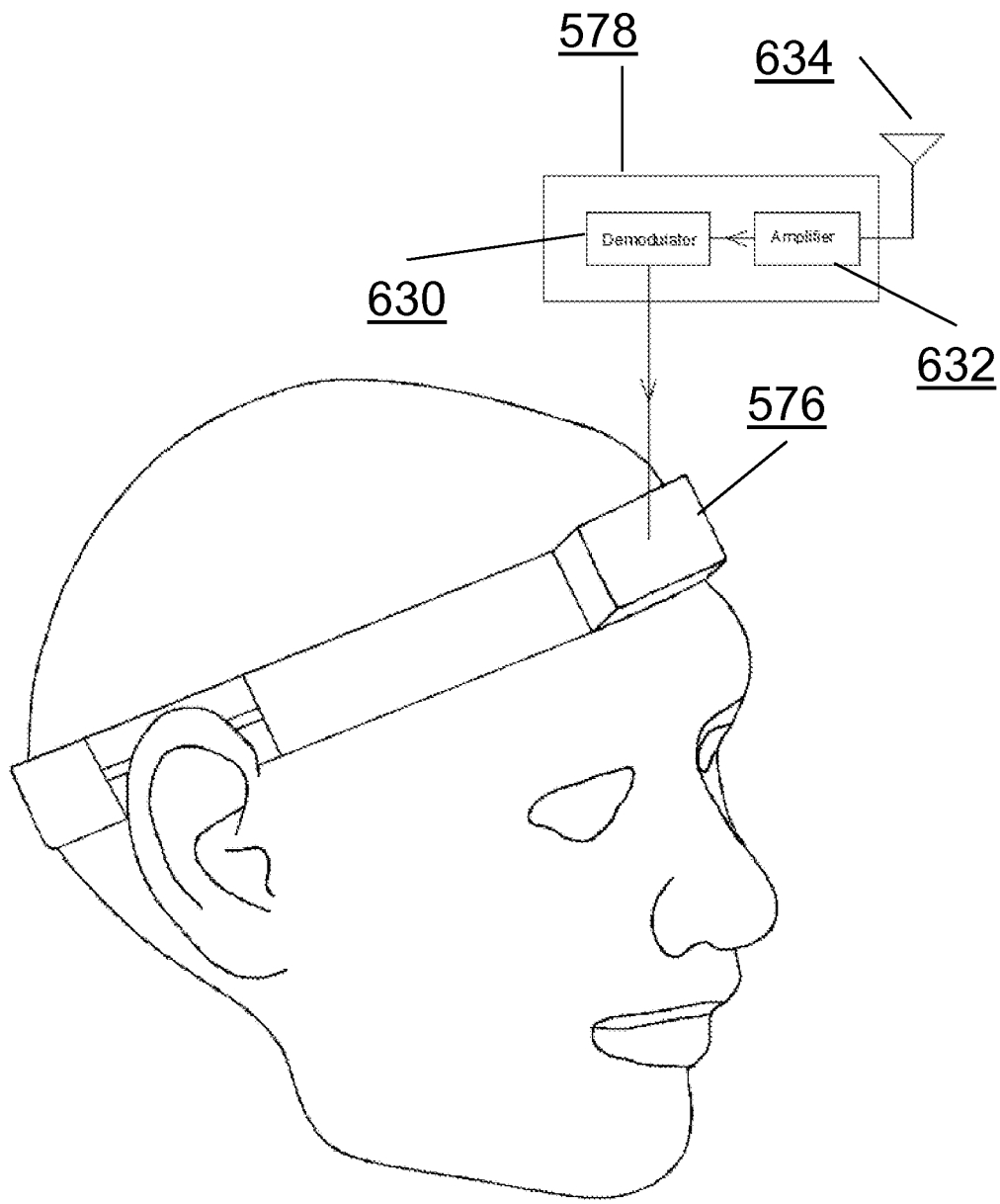
FIG. 9 is a schematic block diagram of the use of a circuit in the electronics module with the real-time microcontroller to add another data stream in synchrony with the other data streams, but this one being received with high temporal precision from the hardware/software associated with the PC.
Figure 10:
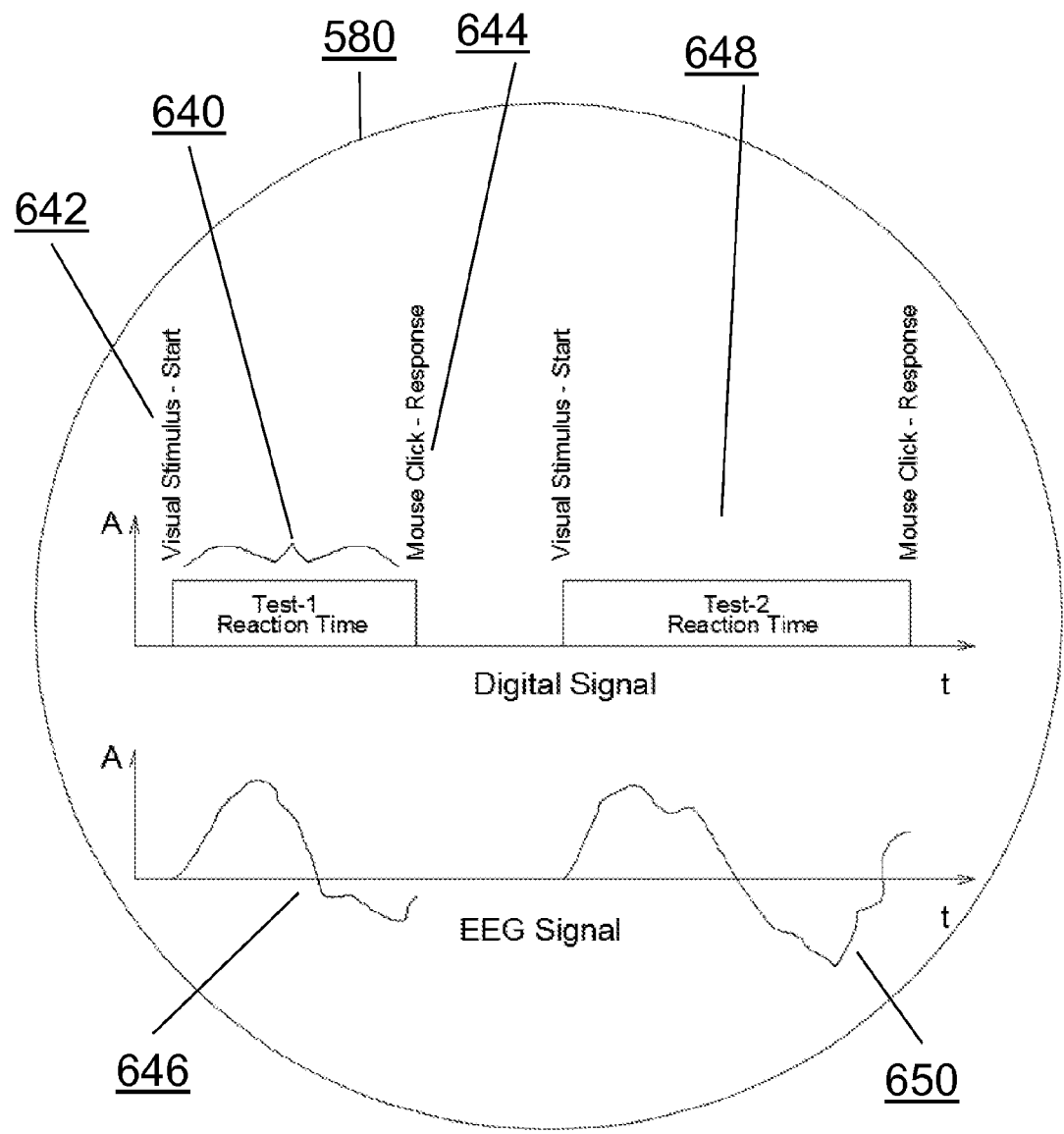
FIG. 10 is a schematic illustration of the temporal synchronization of a PC with a real-time data collection microcontroller with an upper time trace showing the human subject's actions while the lower time trace shows the synchronized signals in an EEG biosensor positioned on the subject's skull.

The gated digital on/off pulse 588 would be used to turn on/off a wireless transmitter 559 which would transmit an On/Off Keyed (OOK) modulated carrier to a matching receiver 578 (FIG. 9). The receiver 578 would amplify 632 and demodulate 630 the carrier thereby presenting a digital replicate 616 (FIG. 8) of the reaction time pulses to the biosensor data acquisition microcontroller. The biosensor data acquisition microcontroller would time-stamp the data with the biosensor data 646 (FIG. 10).

The wireless transmitter/receiver pair could be a radio transmitter operating in the RF spectrum, a pulsed infrared light operating in the infrared spectrum, or an ultrasonic pulse operating in the ultrasonic sound spectrum as follows.

RF Link

The hardware for an RF wireless link may include the LINX Inc., TXM-433-LR RF Transmitter and RXM-433-LR Receiver pair that operates in the 433 MHz RF band. The small sized integrated circuit makes a simple low-parts-count solution for a RF link. http://www.linxtechnologies.com/resources/data-guides/txm-xxx-lr.pdf. Alternate choices include a Silicon Labs SI4010 paired with a ST4313 or a RF Solutions AM110C1-315 operable in the 868 MHz and 915 MHz band as well. Even use of a 2.4 GHz radio transceiver like the Nordic nRF24L01+ can be used in a pair. Bluetooth transceivers, ZigBee, ANT and others are also embodiments of the present invention. Even Wi-Fi modules such as ESP8266 Wi-Fi could be employed in a pair.

Infrared Link

The IR transmitter hardware for an infrared wireless link may include a Vishay Semiconductors TSAL4400 infrared (IR) light emitting diode (LED) operating at an IR wavelength of 940 nm and pulsed on/off via the microcontroller at a carrier frequency of 36 kHz. http://www.vishay.com/docs/81006/tsa14400.pdf. The IR receiver hardware could include, as non-limiting examples, a Vishay Semiconductor TSOP6236 which has a 36 kHz band-pass filter to eliminate background noise. http://www.vishay.com/docs/82463/tsop62.pdf. Also possible would be VS1838 TL and TL1838 or VS1838B universal receiving head.

Ultrasonic Link

The ultrasonic transmitter hardware for an ultrasonic link may include a Murata Electronics MA40S4S ultrasonic transmitter operating at an acoustic frequency of 40 kHz using the microcontroller to generator the 40 kHz carrier. http://www.murata.com/~/media/webrenewal/support/library/catalog/products/k70e.ashx. The ultrasonic receiver hardware could include a Murata Electronics MA40S4R receiver. Alternates pairs of transmitter/receiver in the ultrasonic space include the HC-SR04 transmitter with a US-015 receiver, as well as a TCT40-16T transmitter with a TCT40-16R receiver.

Hardwired Link

The transmission link could also be a hardwired connection between the biosensor headset and the stimulus/response circuitry. In this configuration, optical isolation circuitry would be used to insure patient safety.

Test Number Identification/Calibration

A preamble transmission prior to start of the patient's test could be easily sent by using two or more light sensors attached to the computer screen 570. By lighting an appropriate array of dots in a binary format, the microcontroller could identify which test is about to occur and transmit this information to the EEG data acquisition microcontroller.

Thus, in the embodiment shown in FIG. 4, a system to synchronize a jittery PC with latency 560 with visual display 570 is synchronized with the head worn electronics module 576 on a subject which includes an embedded microcontroller. In this particular implementation, the emitter is a particular region 568 of the visual display 570 which emits light that is received by a photodiode or phototransistor 566 which is connected to an electronic circuit 564 which includes an encoding scheme 562 which wirelessly transmits encoded data to a receiving circuit 578 in the electronics module 576 worn by the subject. In addition, precise timing of mouse clicks in mouse 572 is directly wired via connection 574 as an input to the system through electronic circuit 564.

Figure 5:
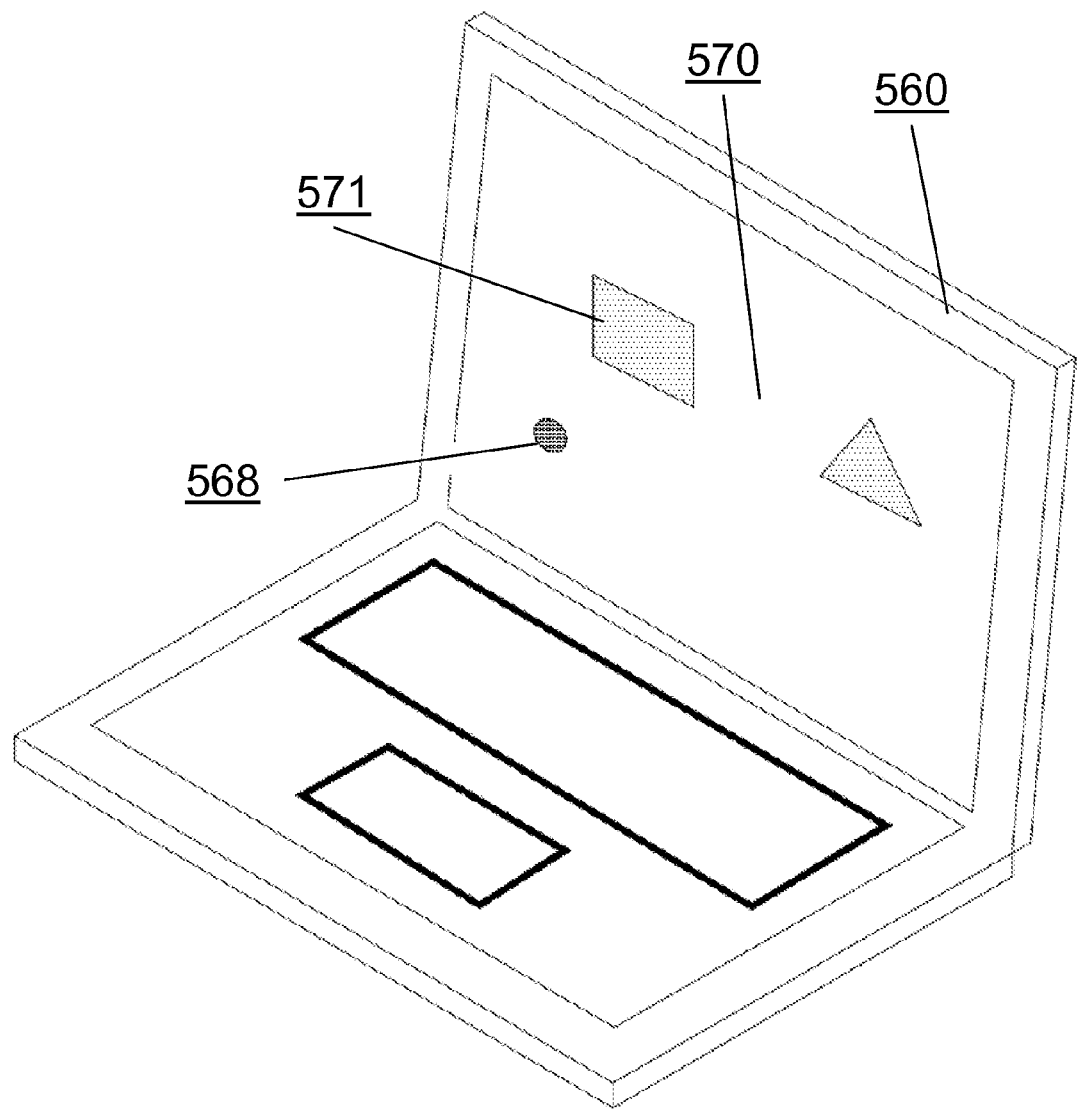
FIG. 5 is a schematic illustration of the PC including the specification of a unique visual stimulus on the computer screen.

Various parts of the system can now be examined in more detail. As shown in FIG. 5, PC 560 with visual screen 570 has a particular region of interest 568 which is responsible for generating the fiduciary light signal which is well synchronized with the other objects 571 displayed and presented as probes to the subject on the PC visual display 570.

Figure 6:
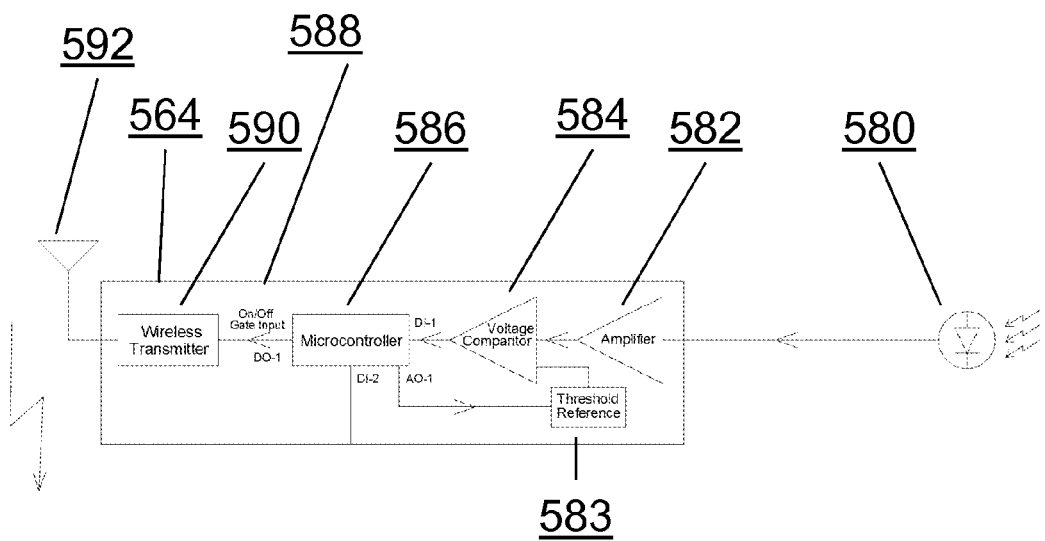
FIG. 6 is a schematic block diagram of an electronic circuit suitable to synchronize the jitter and latency of a PC with a real-time data collection microcontroller based system.

FIG. 6 shows a detail of photodiode or photo resistor 580 which is wired into electronic circuit 564 which consists of amplifier 582 whose output is connected to a voltage comparator 584 which looks at a threshold reference 583 and compares the two in microcontroller 586 who has a gated on off output 588 which moves to wireless transmitter 590 to be output via the antenna 592.

Figure 7:
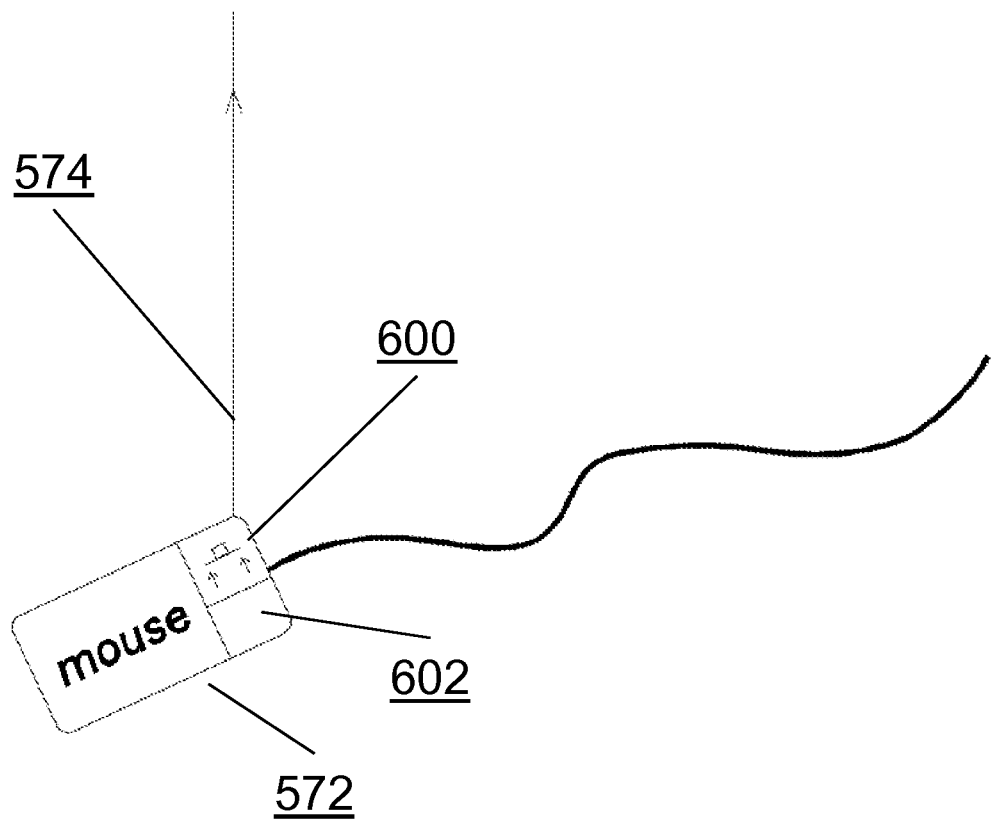
FIG. 7 is a schematic illustration of the use of a fast switch within a computer mouse or other human interface device to enable synchronization and the reduction of jitter and latency of a PC with a real-time data collection microcontroller based system.

FIG. 7 shows a detail of computer mouse 572 which has a high-speed precision switch 600 included in its manufacturing such that the left and right mouse buttons 602 can be encoded via a direct link 574 to either a wired or wireless interface to the subject form embedded micro controller.

FIG. 8 shows a detailed view of the encoding scheme 562 whereby in the upper trace one sees a graphical representation of amplitude as a function of time along the x-axis. To the far left of the upper trace one can see visual stimulus 612 starts and then ends at mouse click response time 614 thereby creating a test one reaction time 610. In the lower trace, one can see the emitter's output in the form of an on and off keyed wireless signal of high relative frequency to enable precise timing in determining the start of the visual stimulus 612 and the end of the mouse click response of the subject 614 thereby encoding the test one reaction time 610 by the presence and duration of the keyed high-frequency wireless signal. To the right in the upper trace, one can see a second test to reaction time 618 and below it its corresponding keyed high-frequency wireless signal 620, which encodes the duration of test to reaction time 618 by the initiation and termination of the keyed high-frequency wireless signal 620.

FIG. 9 provides a more detailed look at a EEG headset or other electronic module 576 worn on the head with a wireless receiver used to capture the wireless reaction time signal for synchronization with EEG data, accelerometer data, pulse oximetry data, and any other head worn biosensor based signals. One can see the receiver circuit 578 which is comprised of a receiving antenna 634 which is attached to amplifier 632 which is demodulated by demodulator 630 within the electronic module worn on the subject 576.

FIG. 10 illustrates how the subject's reaction time information can be precisely synchronized with a biosensor based signal such as an EEG signal in the microcontroller with real time clock. This scheme 580 shows in the upper trace an amplitude on the y-axis as a function of time on the x-axis for the digital signal which is arriving from the subject's interaction with the jittery PC with latency. As before, the presentation of something such as a visual stimulus would start at 642 and the subject would have an event or response here shown as a non-limiting mouse click response 644 thus creating a time difference between the visual stimulation 642 and the response 644 which consists of test one reaction time 640. This digital signal would then be in tight synchronization with the ongoing biosensor based signal 646, shown in the present example as a non-limiting EEG signal. To the right of FIG. 10 in the upper trace one can see a repeat with a longer response test 2 reaction time 648 along with the synchronized and corresponding lower right trace of the biosensor signal 650, in this case an EEG signal.

Figure 11:
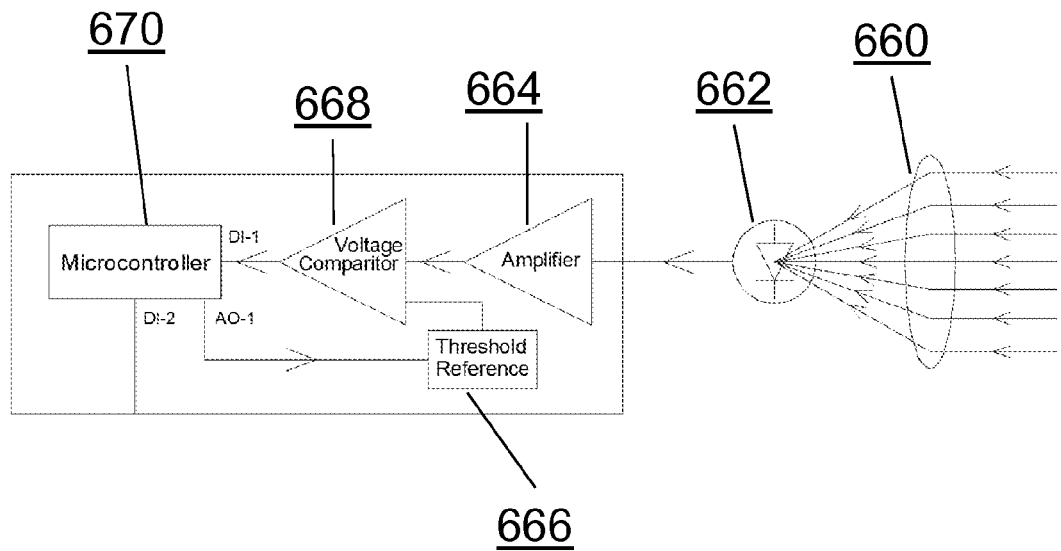
FIG. 11 is a schematic block diagram of a wireless opto-electronic configuration of a light sensor and lens mounted inside the head-positioned electronics module, capturing light from the PC display directly as a source of high precision real-time synchronization data.

In an alternate embodiment, FIG. 11 shows a light sensor 662 and lens 660 mounted inside the EEG headset or subject worn electronics module capturing light directly from the computer LCD or visual display. In this case, the light from the jittery PC with latency emitted from the visual display is directly collected via lens 660 into photodiode or phototransistor 662. The photo diode or photo transistor signal is coupled to amplifier 664 which is connected to voltage comparator 668 along with the threshold reference 666 such that microcontroller 670 can thus determine when the collected light from the jittery PC with latency rises above a preset threshold indicative of the presentation of a probe or stimulate the subject for their response. This embodiment has the advantage that it does not require additional hardware in the vicinity of the jittery PC with latency but has the further requirement that the light which is emitted by the visual display of the jittery PC with latency is being received and can be collected by lens 660.

Figure 12:
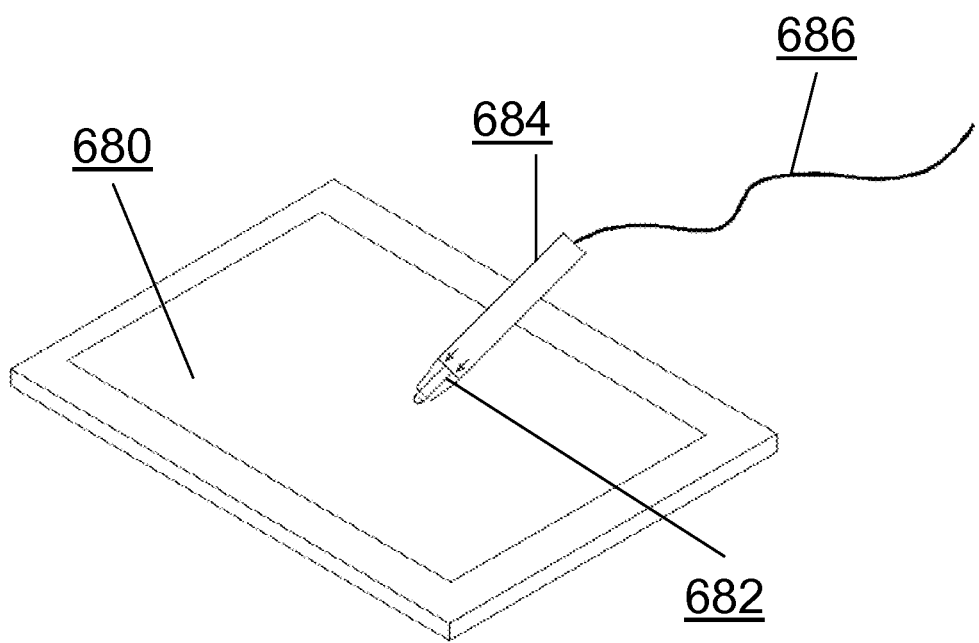
FIG. 12 is a schematic illustration of a fast switch embedded in a stylus or other human interface device to enable a wired synchronization and reduction in jitter and latency between a PC and a remote electronics module consisting of biosensors and a real-time based microcontroller.

FIG. 12 illustrates an alternate embodiment of the present invention which consists not of a computer mouse but instead a special stylus 684 in this case connected with a wire 686, whereby the stylus 684 has a high-speed switch 682 embedded in the tip of the stylus so that each time it is pressed onto the tablet PC or visual display 680 the precise timing is encoded in the opening and closing of the high-speed switch 682. One can appreciate that this human interface device is different than a mouse and can in some instances provide a more natural interaction and thereby better assessment of the relative timing of the subject's response to the stimulation probe on the visual display or auditory stimulation via the soundcard to the subject's auditory cortex.

Acoustic Linkage between Transmitter and Receiver

Figure 13:
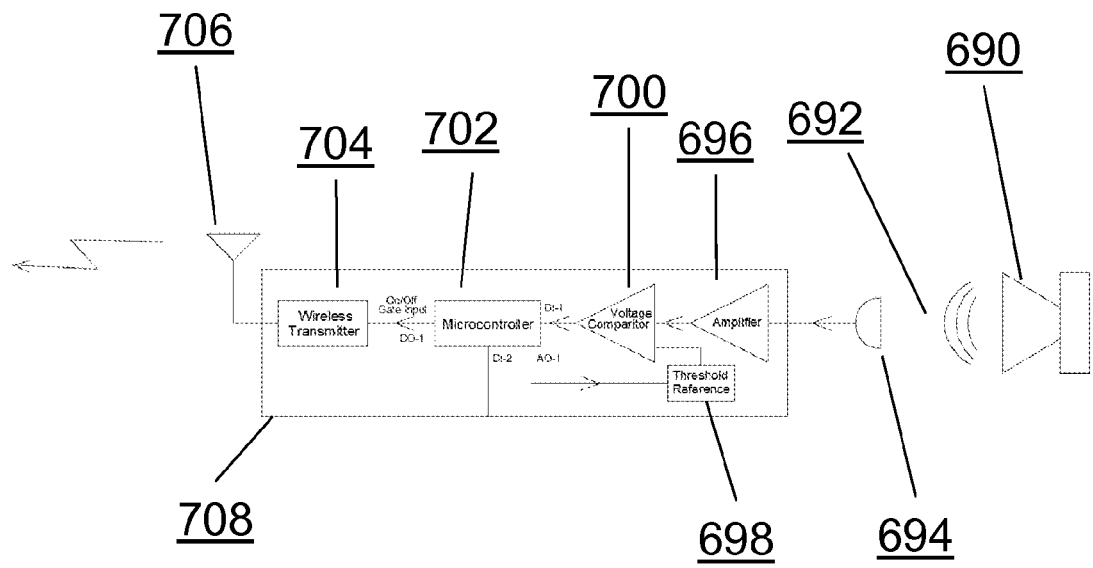
FIG. 13 is a schematic block diagram of a wireless acoustic-electronic configuration of a sound transducer or speaker with a microphone as an additional input to a multimodal biosensor system collected by a remote real-time microcontroller.

The present invention can also be used with other types of stimuli such as an acoustic stimulus. In this configuration, the light-sensor would be replaced with a miniature microphone 694 (FIG. 13) attached to the computer's speaker grill which would signal the exact time the acoustic stimulus was presented to the patient, again independent of the computer's operating system timing jitter. If earbuds are employed rather than a speaker, one can insert a dongle in between the source generating sound card and ear buds. As shown in FIG. 13, audible sound is used as the energy transfer for synchronization. In this case, an audible microphone 694 is included as the receiver in the electronics module worn by the subject or positioned locally on the peripheral PC as the sound is captured from human audible sound generated from the PC speaker 690 functioning as the emitter. More precisely, the computer speaker 690 emits sound waves as the energy source 692 which is received on the human subject by microphone 694 whose output is connected to electronic circuit 708 which includes amplifier 696 which is coupled to voltage comparator 700 with an input threshold reference 698. The output of the voltage comparator 700 then goes to microcontroller 702 which has an on/off gate output which is received by wireless transmitter 704 as an input whose output is generated through antenna 706. The advantage of this embodiment is that the sound generated by the PC speaker 690 is uniformly admitted so that it is easy to be detected by microphone 694 worn by the subject. A potential problem with this approach is the effect of the sound on the central nervous system of the subject.

Figure 14:
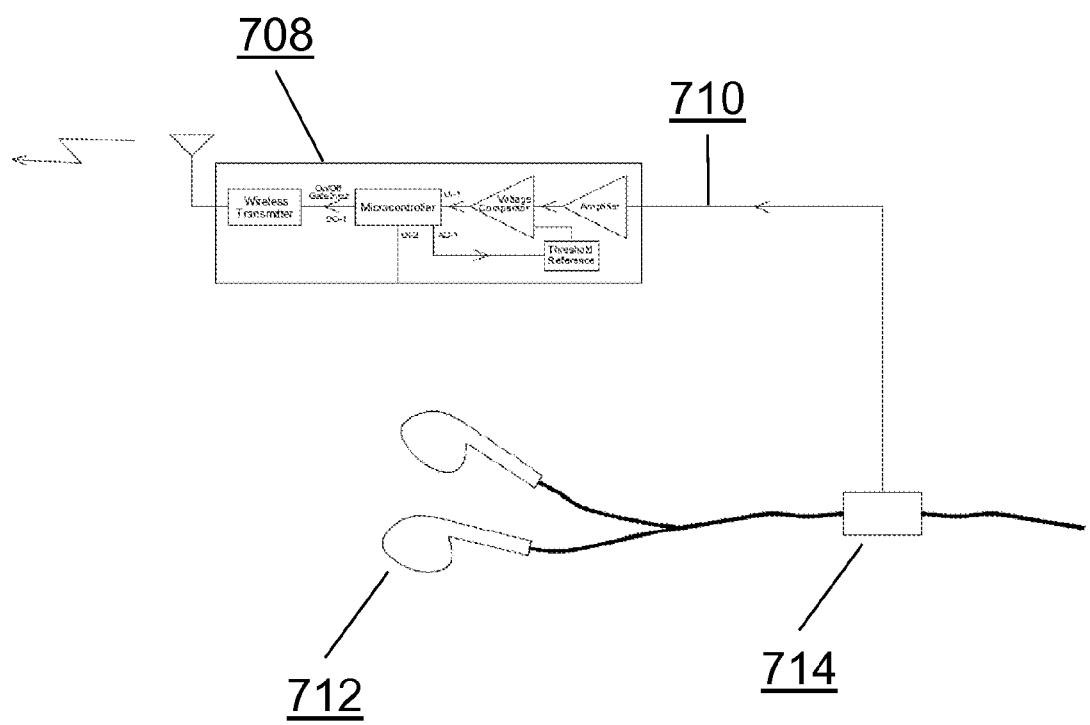
FIG. 14 is a schematic block diagram of a wired acoustic-electronic configuration of a pair of earbuds or other sound transducer connected to a high response frequency or short latency circuit to wirelessly transmit the appearance and disappearance of audio signals in the earbuds or sound source for a human.

In FIG. 14, an alternate embodiment is shown for the detection of audible sound delivered via earbuds. In this embodiment, the wired sound going to earbuds 712 is intercepted at a junction box 714 which divides a second copy of the electrical sound signal via connection 710 which enters electronic circuit 708 of a similar type. In this case, when the sound is quiet, the amplitude relative to the threshold reference will be low and when sound is actually being admitted, the detected signal would be above and this will gate on and off the wireless transmitter in synchrony at high precision and short relative latency to enable a synchronized wireless transmission between the audible stimuli probe of the earbuds 712 and the rest of the biosensor based data being collected by the microcontroller with real-time clock.

Other Types of Response Devices

The present invention can also be used with other patient response devices besides a computer mouse. In FIG. 12, for instance, for a tablet PC 680 the invention could be incorporated into a stylus 684 that has a switch 682 to detect when the stylus touches the screen of the table PC's touchscreen. In another embodiment, the stylus could have two ends which are colored differently to uniquely label each end. Depending on the stimulus presented, either the end colored/labeled with an A could be pressed and the micro-switch contained. To another task, the alternate end labelled B could be pressed, thus differentiating the subject's choices. A cigar shape form factor could be alternatively employed with a tilt or accelerometer within to measure the subject's response. Angular rotation could be picked up via a gyrometer to make a 6 axis rather than just 3 linear axis motion analysis for more subtle refinement of the subject's motion.

Moreover, the response to the stimulus could also be an eye-blink of the Subject. In this arrangement, an EEG signal at positions Fp1 and/or Fp2 would easily pick-up the eye-blink response directly.

Figure 15:
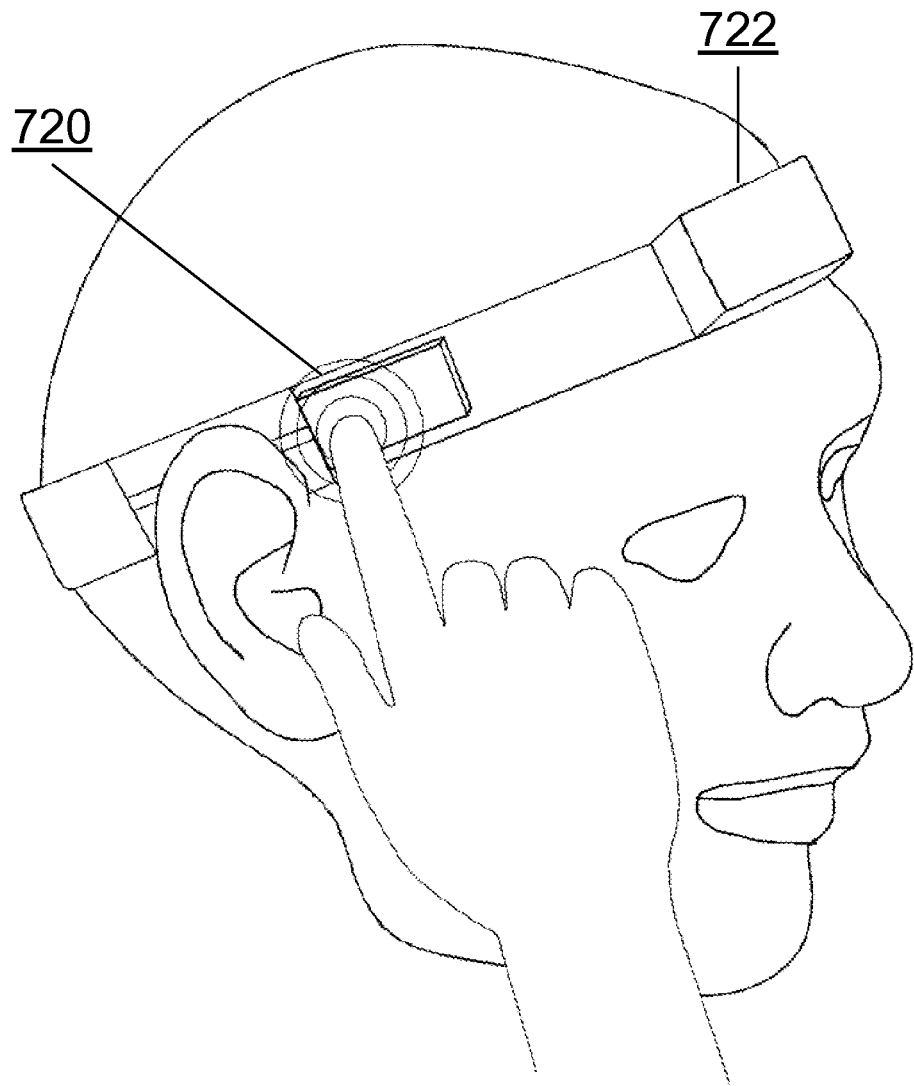
FIG. 15 is a schematic illustration of the use of a local accelerometer or motion processing unit (with possible gyrometer) to enable a human subject to tap or provide other physical mechanical input signals to indicate a response to visual, acoustic or other sensory stimulation or cognitive process.

The response to the stimulus could also be a tilt of the patient's head, as embodied in FIG. 15, if an accelerometer is incorporated into the biosensor headset electronics module 720 or is placed adjacent to it. Gesture detection could also be leveraged whereby a motion processing unit (accelerometer+specialized microcontroller 722) is employed as an event marker such that one physical tap is encoding one type of event while two physical taps in succession would encode a second type of event. More concretely, tap once for right, tap twice for left instead of using a mouse click.

The advantage of this configuration of FIG. 15 is that the subject merely has to tap their head in order to indicate a response to embedded microcontroller 722 indicating what they are hearing, seeing, or other sensory and cognitive input.

Other Encoding Schemes for Binary and Larger Choices

Figure 16:
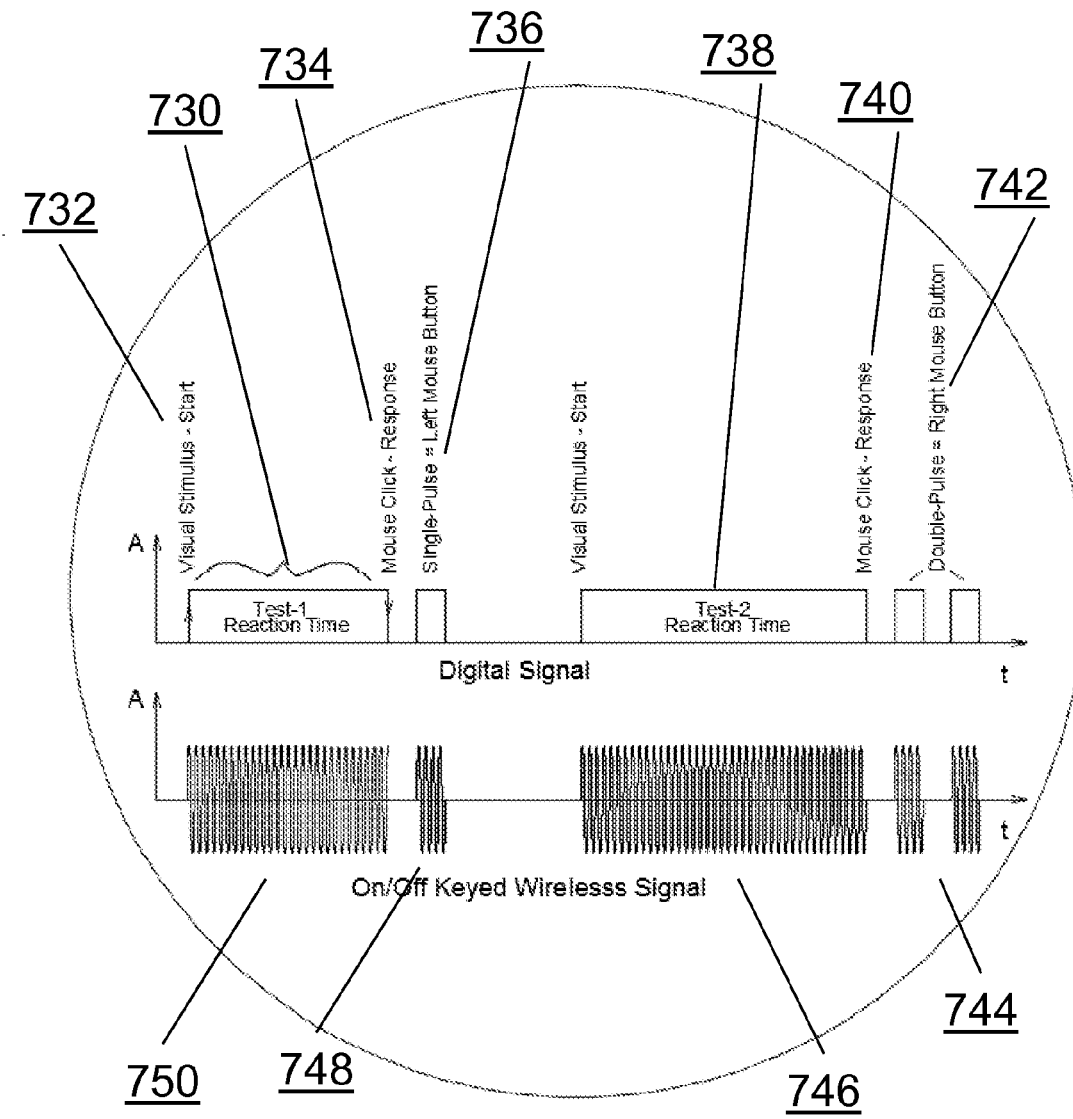
FIG. 16 is a schematic illustration of the temporal synchronization of a PC with a real-time data collection microcontroller with an upper time trace showing the human subject's actions relative to a visual or acoustic stimulus whereby a left mouse click or touch event is registered as a single pulse and a right mouse click or touch event is encoded by a double pulse, while the lower time trace shows the synchronized signals of a high speed oscillator being fed to a wireless transceiver for communication to a transceiver connected to the remote real-time microcontroller collecting data.

FIG. 16 illustrates an alternate embodiment that includes an alternate means of encoding left or right mouse click events or right or left touch screen events into an on/off keyed wireless signal whereby a left mouse click is encoded by a single pulse of output whereas a right mouse click is encoded as a double pulse of output. In this scheme, one can see an upper trace showing amplitude as a function of time of the digital signal and just below it in precise synchronization is the amplitude output is a function of time of the on off keyed wireless signal. When a visual stimulus or auditory stimulus is presented at 732 is started it is perceived by the subject by a mouse click in this case response 734 and the difference in time is shown as test one reaction time 730. At the end of this, if a left mouse button was depressed, a single pulse would be expressed by the digital system 736. In the lower left trace, one can see that the one off keyed wireless system has a high amplitude between the presentation of the stimulus and the subject's mouse response click as shown by 750 and it is subsequently followed by a single pulse of duration output 748. It is this follow-on pulse of output that encodes that it was a left mouse button rather than a right mouse button. Similarly, in the upper trace on the right-hand side one can see test two reaction time 738 which is ended by mouse click response 740 in this case a right mouse button response and so two pulses of fixed width energy 742 are committed after the reaction time. This can be visualized in the lower right-hand trace as the reaction time is encoded in the one off keyed wireless signal 746 with a leading and following edge indicating the start and response to the visual stimulation start in the mouse click response but in this case it is preceded by two pulses of energy 744 thus encoding the fact that it was a right-handed mouse button depression not a left. One of ordinary skill in the art can envision other similar schemes whereby the additional information is encoded either in the frequency of the additional pulses of energy or in the amplitude of the number of pulses of energy or in this case the actual number of discrete pulses of energy.

Those skilled in the art will also appreciate that the invention may be applied to other applications and may be modified without departing from the scope of the invention. For example, the jittery PC with latency described herein may be used in an industrial application and the remote sensors and embedded microcontroller could be on a server, in the cloud, in the electronics module, or on a local PC, tablet PC, smartphone, or custom hand held device. Accordingly, the scope of the invention is not intended to be limited to the exemplary embodiments described above, but only by the appended claims.

What is claimed:

1. A system for synchronizing a PC exhibiting latency of operations and a biosensor enabled microcontroller with real-time clock, comprising:
    a transmitter that transmits a stimulus signal from the PC exhibiting latency;
    an input device indicating the subject's response to the stimulus signal;
    an encoding circuit adapted to encode a difference in time between the stimulus signal and the subject's response to the stimulus signal;
    an emitter adapted to transmit the encoded difference signal representing the subject's reaction time; and
    a complementary receiver adapted to detect the encoded difference signal and including a decoding circuit that decodes the encoded difference signal to determine the subject's reaction time, said receiver providing the subject's reaction time to the microcontroller with real-time clock for synchronization with received biosensor data.

2. A system as in claim 1, wherein the emitter comprises a visible LED, an ultrasonic transducer, an infrared (IR) LED, an audible speaker, audible transducer, a Bluetooth transmitter/transceiver, a Wi-Fi transmitter/transceiver, a ZigBee transmitter/transceiver or AM or FM transmitter/transceiver.

3. A system as in claim 2, wherein the receiver comprises a visible photodiode, visible phototransistor, an ultrasonic receiver/microphone, an infrared (IR) photodiode, an infrared phototransistor, an audible microphone, a Bluetooth receiver/transceiver, a Wifi receiver/transceiver, a ZigBee receiver/transceiver, an AM receiver/transceiver, or an FM receiver/transceiver.

4. A system as in claim 1, wherein the input device is a mouse and the encoding circuit is responsive to the stimulus signal from the transmitter and an input signal from the mouse in response to the stimulus signal.

5. A system as in claim 4, wherein the encoding circuit encodes the difference signal as an on/off keyed wireless signal and provides the encoded difference signal to the emitter for wireless transmission to the complementary receiver.

6. A system as in claim 5, wherein the encoding circuit encodes a left mouse click as one keyed pulse and a right mouse click as two keyed pulses.

7. A system as in claim 1, wherein the complementary receiver is located at an EEG headset of the subject, said EEG headset including said decoding circuit and said microcontroller for synchronizing the subject's reaction time to EEG data collected by said EEG headset.

8. A system as in claim 7, wherein the emitter comprises an audible speaker and the receiver comprises an earbud of the subject, said earbud providing received sound signals to said decoding circuit.

9. A system as in claim 7, wherein the EEG headset includes a finger tap input as said input device.

10. A system as in claim 1, wherein the input device is a stylus and the PC exhibiting latency is a tablet PC.

* * * * *